(12) United States Patent
Li et al.

(10) Patent No.: US 7,763,456 B2
(45) Date of Patent: Jul. 27, 2010

(54) 3D MICRO-SCALE ENGINEERED TISSUE MODEL SYSTEMS

(75) Inventors: Wei Li, Shoreline, WA (US); Hai Wang, Seattle, WA (US)

(73) Assignee: University of Washington, Seattle, WA (US)

( * ) Notice: Subject to any disclaimer, the term of this patent is extended or adjusted under 35 U.S.C. 154(b) by 183 days.

(21) Appl. No.: 11/864,698

(22) Filed: Sep. 28, 2007

(65) Prior Publication Data

US 2008/0102478 A1 May 1, 2008

Related U.S. Application Data (60) Provisional application No. 60/848,263, filed on Sep. 28, 2006.

(51) Int. Cl.
  C12M 3/00 (2006.01)
  C12Q 1/02 (2006.01)
(52) U.S. Cl. ..................... 435/288.5; 435/29
(58) Field of Classification Search .............. None
  See application file for complete search history.

(56) References Cited

U.S. PATENT DOCUMENTS

| | | | |
|---|---|---|---|
| 1,140,548 A | 5/1915 | Vogelsang |
| 3,449,477 A | 6/1969 | Logomasini |
| 3,799,742 A | 3/1974 | Coleman |
| 4,124,529 A | 11/1978 | Jüntgen |
| 4,329,067 A | 5/1982 | Goudy, Jr. |
| 4,426,451 A | 1/1984 | Columbus |
| 4,695,301 A | 9/1987 | Okajima |
| 4,756,884 A | 7/1988 | Hillman |
| 5,037,619 A | 8/1991 | Alagy |
| 5,164,087 A | 11/1992 | Naoi |
| 5,234,587 A | 8/1993 | Allington |
| 5,505,892 A | 4/1996 | Domme |
| 6,036,927 A | 3/2000 | Chatterjee |
| 6,168,948 B1 | 1/2001 | Anderson |
| 6,270,641 B1 | 8/2001 | Griffiths |
| 6,368,871 B1 | 4/2002 | Christel |
| 6,383,422 B1 | 5/2002 | Hoffschmidt |
| 6,418,968 B1 | 7/2002 | Pezzuto |
| 6,672,756 B1 | 1/2004 | Barland |
| 6,729,352 B2 | 5/2004 | O'Connor |
| 6,880,576 B2 | 4/2005 | Karp |
| 6,926,828 B2 | 8/2005 | Shiraishi |
| 6,935,772 B2 | 8/2005 | Karp |
| 6,981,522 B2 | 1/2006 | O'Connor |
| 7,028,536 B2 | 4/2006 | Karp |
| 7,189,368 B2 | 3/2007 | Andersson |
| 7,318,912 B2 | 1/2008 | Pezzuto |
| 7,534,315 B1 | 5/2009 | Singh |
| 2003/0054545 A1 | 3/2003 | Janigro |
| 2003/0198130 A1 | 10/2003 | Karp |
| 2003/0213733 A1 | 11/2003 | Beckham |
| 2004/0149634 A1 | 8/2004 | Hughes |
| 2004/0178143 A1 | 9/2004 | Rogers |
| 2004/0245172 A1 | 12/2004 | Petersen |
| 2005/0087767 A1 | 4/2005 | Fitzgerald |
| 2005/0095602 A1 | 5/2005 | West |
| 2006/0173394 A1 | 8/2006 | Stroock |
| 2008/0102478 A1 | 5/2008 | Li |

FOREIGN PATENT DOCUMENTS

JP  58-150421 A  9/1983

OTHER PUBLICATIONS

Lichtenberg et al. A Multifunctional Bioreactor for Three-Dimensional Cell (Co)-Culture; Biomaterials, vol. 26 (2005) pp. 555-562.*

Nishibori et al. An Interaction Between Human Colon Carcinoma Cells and Hepatocytes Activates Transforming Growth Factor-Beta 1 in Vitro; Cancer Letters, vol. 142 (1999) pp. 83-89.*

Wei et al. Elucidating in Vitro Cell-Cell Interaction Using a Microfluidic Coculture System; Biomedical Microdevices, vol. 8 (2006) pp. 65-71.*

Brannon-Peppas, L., "Polymers in Controlled Drug Delivery," Medical Plastics and Biomaterials 4:34-45, Nov. 1997.

Chapekar, M., "Tissue Engineering: Challenges and Opportunities," Journal of Biomedical Materials Research 53(6):617-620, Nov. 2000.

Freedman, D.H., "The Silicon Guinea Pig," Technology Review, Jun. 1, 2004, pp. 62-68.

Griffith, L.G., "Emerging Design Principles in Biomaterials and Scaffolds for Tissue Engineering," Annals of the New York Academy of Sciences 961:83-95, 2002.

(Continued)

*Primary Examiner*—Rebecca E. Prouty
*Assistant Examiner*—Paul C. Martin
(74) *Attorney, Agent, or Firm*—Christensen O'Connor Johnson Kindness PLLC (57) ABSTRACT

A polymeric chip having at least one three-dimensional porous scaffold, a microfluidic channel inlet to the porous scaffold, and a microfluidic channel outlet from the porous scaffold. In one embodiment, the polymeric chip has two three-dimensional porous scaffolds: one scaffold comprises liver cells and the other scaffold comprises cancer cells. The chip can be used as a multi-organ tissue model system.

21 Claims, 9 Drawing Sheets

OTHER PUBLICATIONS

Krause, B., et al., "Open Nanoporous Morphologies from Polymeric Blends by Carbon Dioxide Foaming," Macromolecules 35(5):1738-1745, Jan. 2002.

Langer, R., and J.P. Vacanti, "Tissue Engineering," Science 260(5110):920-926, May 1993.

Sefton, M.V., "Functional Considerations in Tissue-Engineering Whole Organs," Annals of the New York Academy of Sciences 961:198-200, Jun. 2002.

Steele, B.C.H., and A. Heinzel, "Materials for Fuel-Cell Technologies," Nature 414(6861):345-352, Nov. 2001.

Wang, X., et al., "A Method for Solvent-Free Fabrication of Porous Polymer Using Solid-State Foaming and Ultrasound for Tissue Engineering Applications," Biomaterials 27:1924-1929, Oct. 2005.

Yang, P., et al., "Hierarchically Ordered Oxides," Science 282(5397):2244-2246, Dec. 1998.

* cited by examiner

3D MICRO-SCALE ENGINEERED TISSUE MODEL SYSTEMS

CROSS-REFERENCE TO RELATED APPLICATION

This application claims the benefit of Provisional Application No. 60/848,263, filed Sep. 28, 2006, which is incorporated herein by reference in its entirety.

STATEMENT OF GOVERNMENT LICENSE RIGHTS

This invention was made with Government support under Contract No. 0348767, awarded by the National Science Foundation. The Government has certain rights in the invention.

BACKGROUND

Drug discovery and development is a complex process to screen compounds based on toxicity and efficacy. Once potential drugs are identified, a series of in vitro and in vivo studies are conducted. Most in vitro studies are done using cell cultures in Petri dishes or test tubes. Following in vitro studies, in vivo studies are carried out by using animal models.

Animal models have been used extensively in drug discovery and development. However, using animal models for drug tests is expensive. In addition, animal studies often yield inaccurate and misleading results because there are differences in human and animal metabolic systems. An effective drug on animals may not be effective on humans. On the other hand, a good compound could be excluded because of the choice of an inappropriate animal species. Therefore, there is a need for a drug screening model system that is cost effective and would provide accurate prediction on a compound activity, absorption, and elimination in humans.

The inaccuracies in using an animal model to predict human responses, safety, and efficacy of a compound indicate that extrapolation from animals to humans has risks. The safety of a drug candidate is extensively studied in laboratory animals before it can be approved for clinical studies. Even though extrapolation from animal model to humans works for most patients, individual variability may cause response differences in different patients. Therefore, there is a need for a drug screening model system that minimizes the extrapolation risk from animals to humans and offers a more accurate prediction on a compound activity and toxicity at an individual patient level.

There is currently no quick, reliable way to predict whether an experimental compound will have toxic side effects on humans. One solution is the development of model systems that closely mimic the complex environment and interaction of human organ systems. In order to mimic what happens to experimental drugs in vivo, microfluidic systems lined with living cells have been developed to simulate human and animal organ systems. A known "silicon Guinea pig" device represents an attempt to mimic living organisms on a silicon microchip. With various chambers and channels simulating the organs and circulatory systems, the silicon Guinea pig has major organ functions of a live Guinea pig and can be used for drug toxicity studies. Experimental drugs can be injected into imitation blood coursing through the chambers lined with living cells. By detecting the chemical reactions happening in these chambers, it is possible to predict if the experimental drug will have a toxic effect when given to an actual human.

Following the same idea, a physiological model of a liver has been developed to study viral infection of human hepatocytes. The main component of this model is an array of micro wells that were created by deep reactive ion etching of a silicon wafer. The well array is combined with a cell-retaining filter and supported in a bioreactor housing designed to deliver a continuous perfusate across the top of the array and through the wells. A feature of the bioreactor is the distribution of cells into many tiny tissue units in the micro wells that are relatively uniformly perfused with culture medium.

Despite the need in drug development, the above microdevices are all silicon based, with micro wells and chambers for cell culturing. With these types of structures, the cells tend to line the bottom and sidewalls of the well or chamber to form two-dimensional monolayers, instead of truly 3D (three-dimensional) tissue constructs. These two-dimensional aggregates may not have normal tissue architecture to perform tissue specific functions, therefore, fail to provide an accurate model system for the tissue.

Therefore, there is a need for a model system that would provide three-dimensional tissue constructs and offer an inexpensive alternative to animal models for drug discovery and development. The present invention seeks to fulfill these needs and provides further related advantages.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a polymeric chip.

In one embodiment, the polymeric chip comprises at least one porous scaffold in the chip, wherein the porous scaffold includes a first surface and a second surface, and wherein the first surface is opposite from the second surface; a first microfluidic inlet channel, wherein the first microfluidic inlet channel is in fluid connectivity with the first surface of the porous scaffold; and a second microfluidic outlet channel, wherein the second microfluidic outlet channel is in fluid connectivity with the second surface of the porous scaffold. The surface can be the entire area defined by either the upper or lower perimeter of the porous scaffold. The first porous scaffold can have a plurality of first living cells, such as liver cells, and the second porous scaffold can have a plurality of second living cells, such as cancer cells.

In one embodiment, the polymeric chip comprises two or more porous scaffolds in the chip, wherein each porous scaffold includes a first surface and a second surface, and wherein the first surface is opposite to the second surface; a first microfluidic inlet channel, wherein the first microfluidic inlet channel is in fluid connectivity with the first surface of each porous scaffold; and a second microfluidic outlet channel, wherein the second microfluidic outlet channel is in fluid connectivity with the second surface of at least one porous scaffold. The surface can be the entire area defined by either the upper or lower perimeter of the porous scaffold. The first porous scaffold can have a plurality of first living cells, such as liver cells, and the second porous scaffold can have a plurality of second living cells, such as cancer cells.

The second microfluidic outlet channel can be in fluid connectivity to the second surface of each porous scaffold. Alternatively, the polymeric chip can further comprise a third microfluidic outlet channel, wherein the third microfluidic outlet channel is in fluid connectivity to the second surface of at least one porous scaffold.

In one embodiment, the polymeric chip comprises at least one porous scaffold in the chip, wherein the porous scaffold includes a first surface and a second surface, and wherein the first surface is opposite from the second surface; a first microfluidic inlet channel, wherein the first microfluidic inlet channel is in fluid connectivity with the first surface of the porous scaffold; and a second microfluidic outlet channel, wherein the second microfluidic outlet channel is in fluid connectivity with the second surface of the porous scaffold. The surface can be the entire area defined by either the upper or lower perimeter of the porous scaffold. The first porous scaffold can have a plurality of first living cells, such as liver cells, and the second porous scaffold can have a plurality of second living cells, such as cancer cells.

In one embodiment, at least one scaffold on the polymeric chip includes a well. The scaffold having a well may be formed from a lower section surrounded by upright walls to form a cavity in the middle.

In another aspect, the present invention provides a method for assaying a compound activity.

In one embodiment, the method comprises the steps of (a) providing a polymeric chip, wherein the polymeric chip comprises a first porous scaffold in the chip; a second porous scaffold in the chip, which is separated from the first porous scaffold; a first microfluidic channel connecting the first porous scaffold to the second porous scaffold; a second microfluidic channel inlet to the first porous scaffold; and a third microfluidic channel outlet from the second porous scaffold; (b) seeding a plurality of first living cells in the first porous scaffold to provide a first cell culture; (c) seeding a plurality of second living cells in the second porous scaffold to provide a second cell culture; (d) dissolving a compound in a cell culture medium to provide a liquid medium; (e) flowing the liquid medium sequentially through the second microfluidic channel inlet, the first cell culture, the first microfluidic channel, the second cell culture, and the third microfluidic channel outlet to provide an assay solution.

In one embodiment, the first cell culture comprises liver cells and the second cell culture comprises cancer cells.

In one embodiment, the method further comprises analyzing the second cell culture to determine the inhibitory activity of the compound on the cancer cells. In one embodiment, the method further comprises analyzing the assay solution.

In one embodiment, the method comprises the steps of (a) providing a polymeric chip, wherein the polymeric chip comprises at least one porous scaffold in the chip, wherein the porous scaffold includes a first surface and a second surface, and wherein the first surface is opposite from the second surface; a first microfluidic inlet channel, wherein the first microfluidic inlet channel is in fluid connectivity with the first surface of the porous scaffold; and a second microfluidic outlet channel, wherein the second microfluidic outlet channel is in fluid connectivity to the second surface of the porous scaffold; (b) seeding a plurality of living cells in the porous scaffold to provide a cell culture; (c) dissolving a compound in a cell culture medium to provide a liquid medium; (d) flowing the liquid medium through the first microfluidic inlet channel, the cell culture, and the second microfluidic outlet channel to provide an assay solution.

The cell culture can include liver cells, cancer cells, or both stromal cells and cancer cells.

In the embodiments described above, the scaffolds include microcellular pores forming a three-dimensional structure. The pores can have an average diameter of about 50 μm to about 200 μm. The pores can be interconnected open-celled pores. Where two or more scaffolds are provided, each scaffold can have similar pore sizes or the same.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A and 5B show a representative polymeric chip in accordance with a second embodiment of the present invention, a two-organ chip design, wherein FIG. 5A is the top view of the chip and FIG. 5B is the bottom view of the chip;

FIGS. 10A and 10B show the results of live/dead staining of smooth muscle cells on porous poly(methyl methacrylate) scaffolds to determine cell viability, wherein FIG. 10A shows the staining results on the porous scaffold with average pore size diameter of 200 μm, and FIG. 10B shows the staining results on the porous scaffold with average pore size diameter of 70 μm.

DETAILED DESCRIPTION OF THE INVENTION

Figure 1:
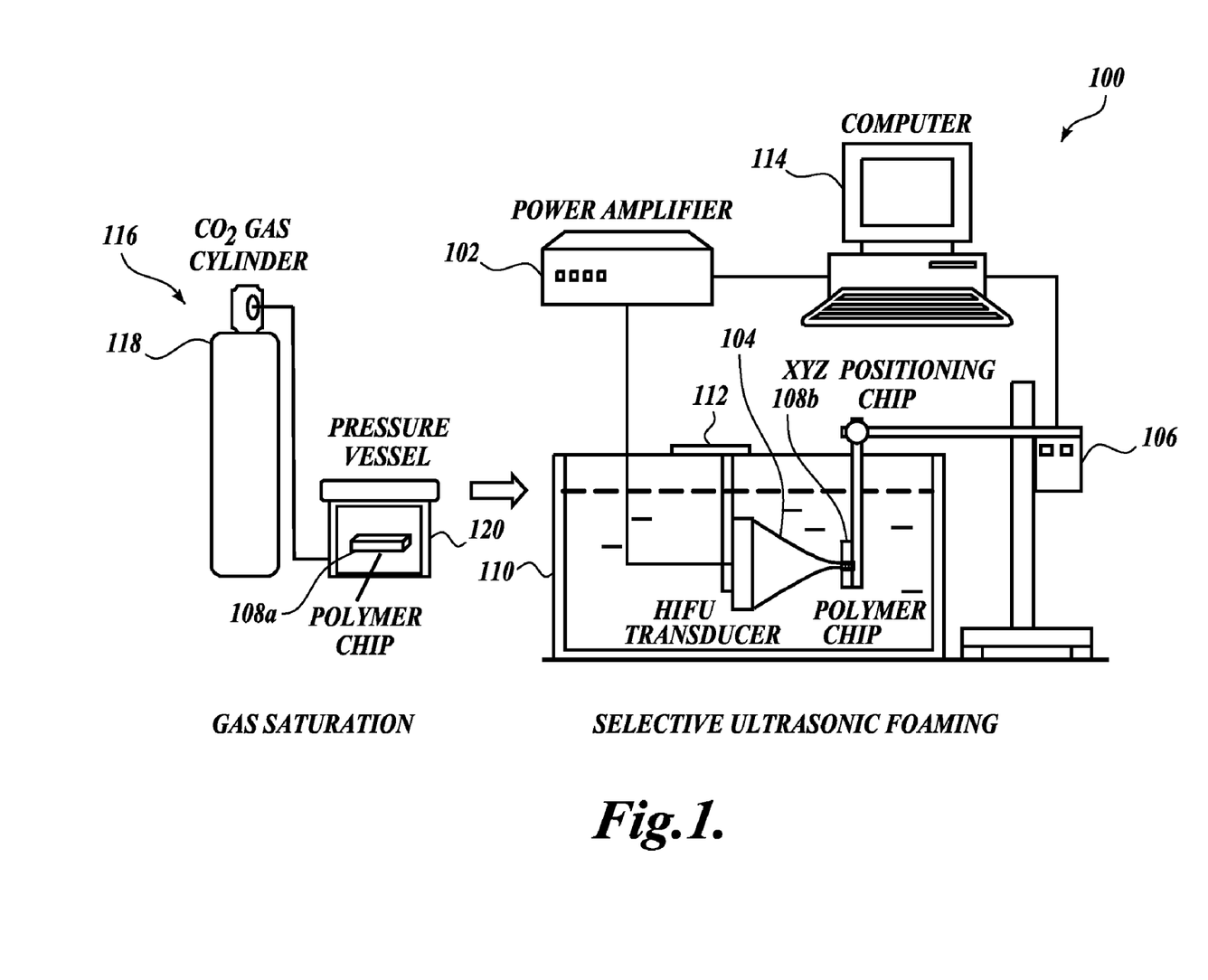
FIG. 1 is a schematic illustration of a system for selectively producing a porous scaffold on a polymeric chip with high intensity ultrasound energy.
Figure 2:
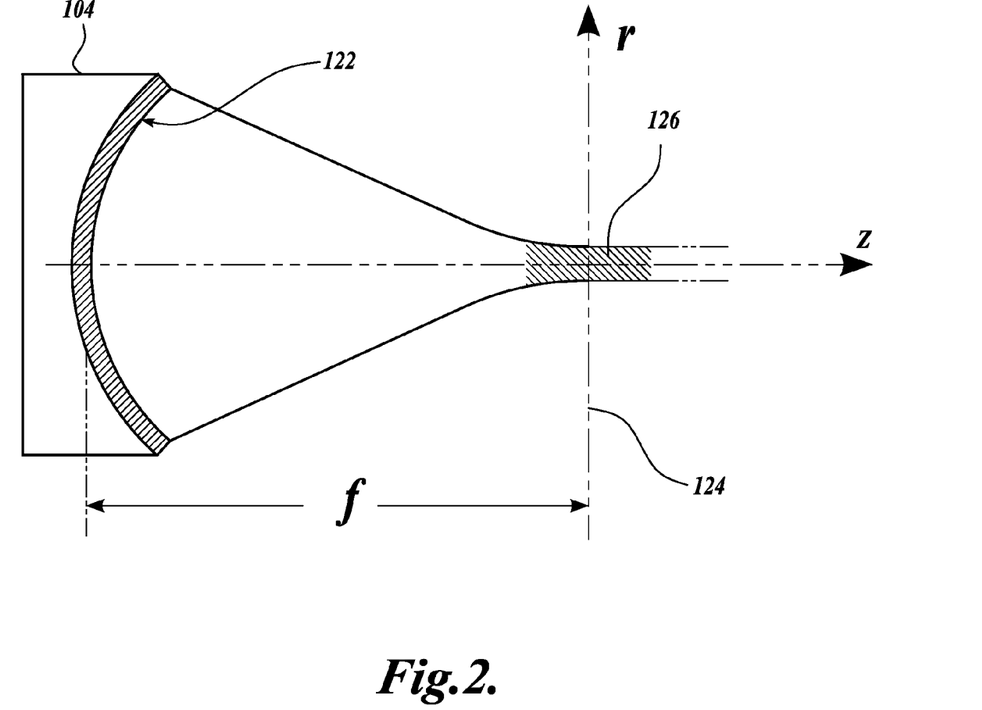
FIG. 2 is a schematic illustration of a focusing ultrasound device.

Illustrated in FIG. 1 is a high intensity focused ultrasound (HIFU) system 100 that can be used to make the polymeric chip of the present invention. The system 100 includes a high intensity focusing ultrasound transducer 104 connected to a power amplifier 102. Referring to FIG. 2, a schematic close-up illustration of the high intensity focusing ultrasound transducer 104 is illustrated. The high intensity focusing ultrasound transducer 104 includes a focusing substrate 122 having a concave surface that focuses ultrasound energy into a concentrated focal zone 126. The focal length of the high intensity focusing ultrasound transducer 104 is denoted by "f." The focal plane is denoted by "r." Preferably, when a polymeric chip is insonated with ultrasound energy, the polymeric chip is located anywhere in the focal zone 126. The high intensity focusing ultrasound transducer 104 produces high intensity ultrasound waves or energy that can be focused so that the focal plane can be targeted on a translation stage of a positioning system 106. The positioning system 106 includes means to move the translation stage in three directions. Those directions being the x and y direction in the focal plane and in the z direction forwards and rearwards of the focal plane. A gas impregnated polymeric chip 108b is placed at or on the translation stage at or near the focal plane of the transducer 104. The polymeric chip 108b is in the target area of the high intensity focusing ultrasound transducer 104. As can be appreciated, the polymeric chip 108b can be moved in the x, y, and z directions so that any location on the polymeric chip 108b can be exposed to the ultrasound energy produced by the high intensity focusing ultrasound transducer 104. The high intensity focused ultrasound energy can be focused on the surface of the polymeric chip 108b or internally in the polymeric chip 108b and at any thickness within the chip. The high intensity focusing ultrasound transducer 104 and the polymeric chip 108b are located in a tank 110 of distilled water for ultrasound propagation. The high intensity focusing ultrasound transducer 104 is stabilized by a support arm 112 connected to the high intensity focusing ultrasound transducer 104. The power amplifier 102 is connected to, and thereby, controlled by a computer 114. Computer 114 may be any one of a variety of devices including, but not limited to, personal computing devices, server-based computing devices, mini and mainframe computers, laptops, or other electronic devices having a type of memory. The computer 114 may include a processor, memory, computer-readable medium drive (e.g., disk drive, a hard drive, CD-ROM/DVD-ROM, etc.) that are all communicatively connected to each other by a communication bus. The computer 114 may also include a display and one or more user input devices, such as a mouse, keyboard, etc. Applications for running the system 100 may be stored in memory in the computer 114. Applications may be described in the context of computer-executable instructions, such as program modules being executed by the computer 114. Such applications may be used to control the amount of power from the power amplifier 102 passed to the high intensity focusing ultrasound transducer 104, and also to control the position of the polymeric chip 108b in relation to the focal plane or focal point of the high intensity focusing ultrasound transducer 104 by controlling the movement of the positioning system 106. To this end, the computer 114 is also connected to, and thereby communicates with, the positioning system 106. The computer 114 can issue commands to the positioning system 106 that permit the polymeric chip 108b to be moved in any direction in the xy plane and at any speed. Additionally, the computer 114 can issue commands to the positioning system 106 to move the polymeric chip 108b in the z direction so as to move the polymeric chip 108b to be within the focal plane or forward or rearward of the focal plane of the high intensity focusing ultrasound transducer 104.

A gas-saturation system 116 includes a gas cylinder 118 connected to a pressure vessel 120. The pressure vessel 120 receives gas and can include pressure regulating means to control the gas pressure within the interior of the pressure vessel 120. The pressure vessel 120 may also include timing means to keep track of the time at a given pressure. The pressure vessel 120 can be used to hold a polymeric chip 108a for a given time and at a given pressure. The gas-saturation system 116 is used to impregnate the polymeric chip 108a with the gas. In one embodiment, the pressure used to impregnate polymeric chip 108a may be in the range of 2 MPa to 10 MPa at room temperature. Additionally, the pressure vessel 120 may be opened to the atmosphere in order to allow gas to desorb from the polymeric chip 108a. Once the polymeric chip 108a has been impregnated with gas from gas cylinder 118, the polymeric chip 108a may be fully saturated with gas or partially saturated with gas. The polymeric chip 108a may additionally undergo desorption of gas for a given period of time at atmospheric pressure. This allows for a quicker method of achieving a desired gas concentration for partial saturation of the polymeric chip 108a. For example, the polymeric chip 108a may be impregnated with gas to full saturation at a high pressure. Thereafter, the pressure vessel 120 may be opened to atmosphere to allow the polymeric chip 108a to desorb gas to bring the saturation level to less than full saturation. This achieves a quicker low gas concentration level in the polymeric chip 108a as compared to initially impregnating the polymeric chip 108a with gas at a lower pressure. From the pressure vessel 120, the polymeric chip 108a is transferred to the arm of the positioning system 106 and may be insonated with high intensity focused ultrasound energy to create a localized porous scaffold within the polymeric chip 108b. One or more areas of the polymeric chip 108b may be insonated with high intensity focused ultrasound energy to create one or more localized and separated areas of porous scaffolds. The porous scaffolds are formed from and are the same material as the polymeric chip 108b and can be interior to or on the surface of the polymeric chip 108b. Furthermore, one or more porous scaffolds can be arranged on the chip in any configuration desirable by controlling the positioning system 106. This allows the creation of porous scaffolds that can be separated and distinct from each other within the same polymeric chip 108b. This is possible because of the polymeric chip 108b being mounted to the translation stage of the positioning system 106, and further, the computer 114 can control the start and stop of insonation of high intensity ultrasound energy to permit selective foaming in any desired location on the polymeric chip 108b. It is further possible to control one or more variables that influence the pore size diameter of the pores in the porous scaffolds and ensure the pores are interconnected open-celled pores. These variables include but are not limited to controlling the gas pressure in the pressure vessel 120, controlling the time that the polymeric chip 108a is exposed to gas under pressure, controlling the time that the polymeric chip 108a is allowed to desorb gas after gas impregnation, controlling the power of the high intensity focused ultrasound transducer 104, controlling the speed that the polymeric chip 108b is moved with respect to the focused beam of ultrasound energy, and controlling the distance of the polymeric chip 108 with respect to the focal plane or focal point. For producing interconnected open-celled pores, the method includes providing a polymeric chip having a gas concentration of 3-5% by weight. This concentration may be obtained by removing the polymeric chip 108a from the pressure vessel 120 before equilibrium is reached, or alternatively, the polymeric chip 108a may be fully saturated, and then allowed to desorb gas to achieve the desired partial saturation and gas concentration.

A method of making a scaffold having micro cellular pores in accordance with one embodiment of the invention includes impregnating a polymeric chip 108 with gas, followed by applying high intensity focused ultrasound energy onto the gas-impregnated chip. In the gas impregnation step, the polymeric chip 108a is placed into the high-pressure vessel 120 filled with an inert gas, such as nitrogen or carbon dioxide. Over time, the gas molecules dissolve into the polymeric chip 108a so that the chip 108a becomes gas-impregnated. Depending on the gas pressure and the impregnation time (the time that the chip 108a remains in the pressure vessel 120), the final gas concentration in the impregnated polymeric chip 108a can be controlled. In a subsequent step, the gas-impregnated polymeric chip 108a is retrieved from the pressure vessel and mounted on a computer controlled XYZ stage for ultrasonic insonation with the high intensity focusing ultrasound transducer 104. Because of the heating and implosion effects induced by ultrasound waves or energy, the gas-impregnated polymeric chip 108b becomes thermodynamically unstable and undergoes phase separation to generate a scaffold having microcellular pores.

The high intensity focused ultrasound polymer foaming effect happens based on two ultrasound related processes: high intensity focused ultrasound heating and high intensity focused ultrasound cavitation. When the polymeric chip is under ultrasound insonation, part of the acoustic energy will be deposited into (or absorbed by) the polymer matrix during the sound wave propagation. The amount of the acoustic energy dissipation depends on the properties of material and the sound wave such as the attenuation coefficient and the ultrasound frequency, and in turn causes the ultrasound heating effect. Besides the heating effect, high intensity focused ultrasound has a cavitation effect in a viscous fluid. High intensity focused ultrasound cavitation happens during the negative cycle of sound pressure, under the conditions that (a) the local acoustic pressure is beyond a certain pressure threshold, and (b), the existence of tiny cavities in the medium which serve as cavitation nuclei.

Figure 3:
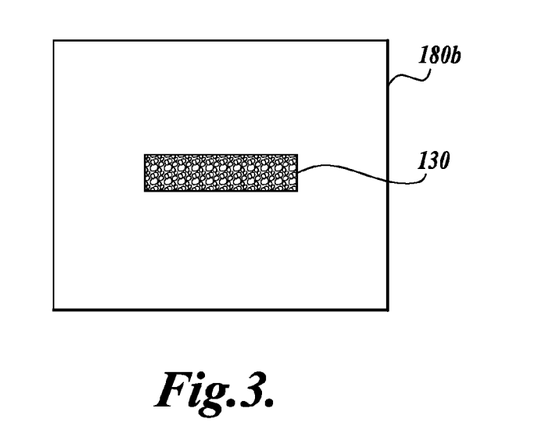
FIG. 3 is a schematic illustration of a representative polymeric chip.

Referring to FIG. 3, a diagrammatical illustration of a polymeric chip 180b with a single localized region of a porous scaffold 130 is illustrated. However, the polymeric chip 108b can have any number of porous foam region such as 130. Using the selective foaming method described herein, the localized region of microcellular porous scaffold 130 can be created in or on any location of the polymeric chip 180b. Regions as small as 1 mm on a side may be produced using the selective high intensity focused ultrasound method described. Furthermore, the polymeric chip 180b and the porous scaffold 130 is the same monolithic material so that the scaffold 130 is formed from the polymeric chip 180b. The scaffold 130 includes pores having an average diameter of 50 µm to 200 µm. The average diameter of the pores, D, is calculated as $$D = \frac{\sum_{i=1}^{N} \sqrt{4 \times A_i / \pi}}{N}$$

where $A_i$ is the area of $i^{th}$ pore and N is the total number of the pores measured from a scanning electron microscopy (SEM) image of a cross section of the foamed region. The polymeric chip 108b is a thermoplastic polymer such as, but not limited to poly(lactic acid), poly(lactic-co-glycolic acid), poly(methyl methacrylate), or polystyrene. These polymers are either biocompatible or biodegradable materials and are useful for many medical or biological applications.

The above described system 100 and method may be used to make porous scaffold in polymeric chips further described below.

Accordingly, in one aspect, the present application provides a polymeric chip for assaying a compound activity.

Figure 4:
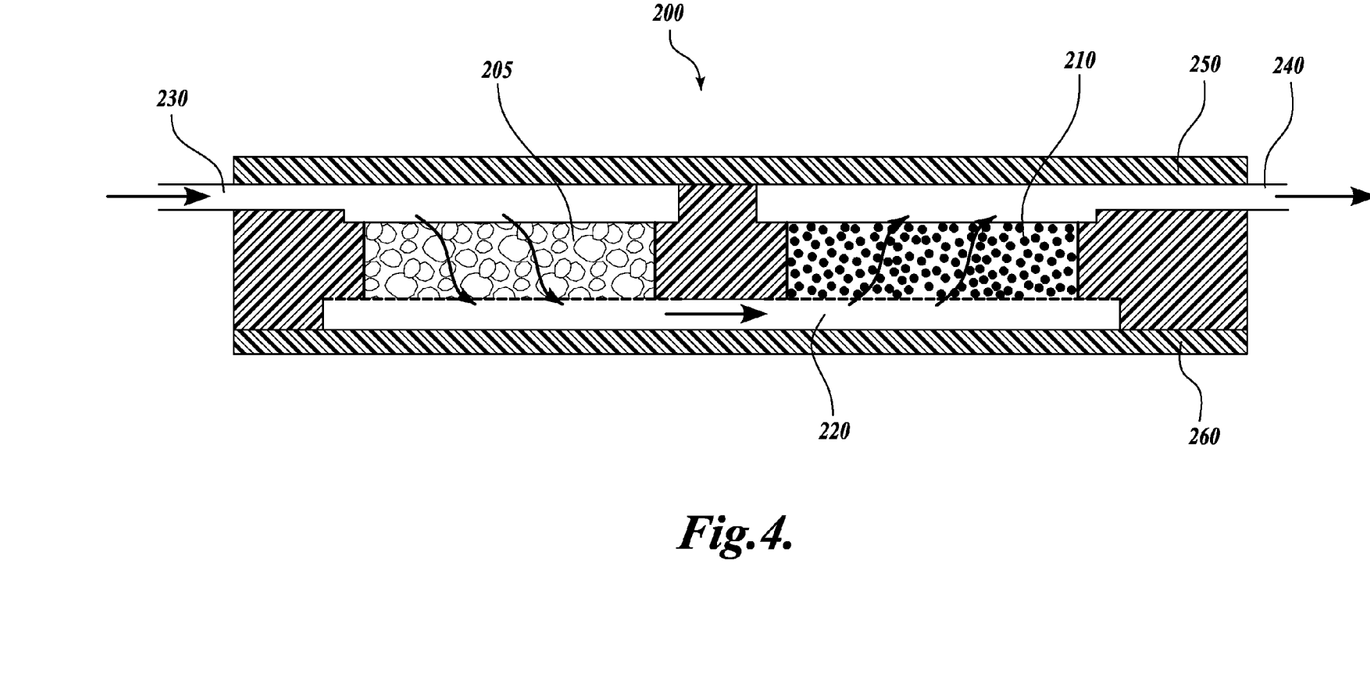
FIG. 4 shows a representative polymeric chip in accordance with one embodiment of the present invention including a schematic design of a liver metabolism chip having perfusion to simulate blood flow.
Figure 8:
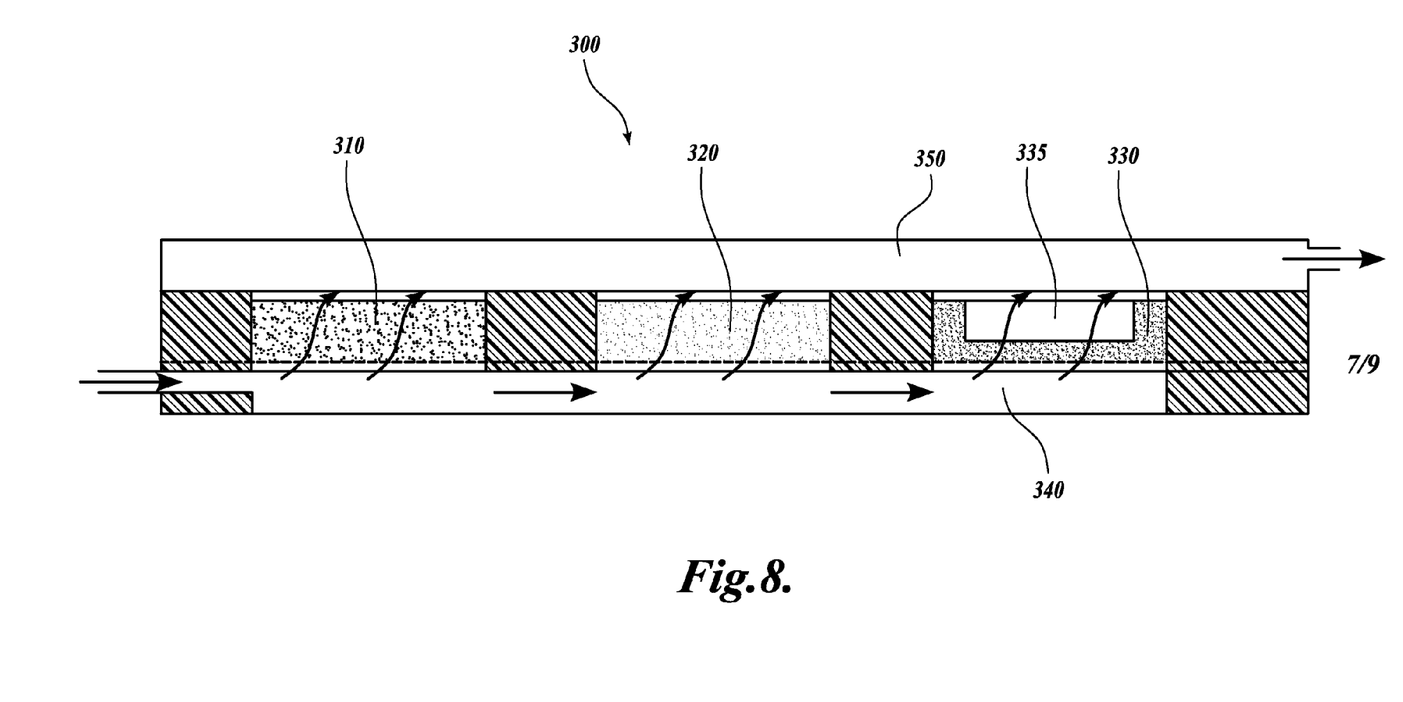
FIG. 8 is a schematic illustration of the polymeric chip shown in FIG. 7, wherein the culture medium inflow is from the bottom so that the scaffold can be submerged in the culture medium.

In one embodiment, the polymeric chip includes at least one porous scaffold in the chip, wherein the porous scaffold includes a first surface and a second surface, and wherein the first surface is opposite from the second surface. For example, as illustrated in FIGS. 4 and 8, the first surface can be the entire upper or lower surface defined by the perimeter of the porous scaffold and the second surface is opposite of the first surface, which is also defined by the perimeter of the porous scaffold. The porous scaffold has a first microfluidic inlet channel, wherein the first microfluidic inlet channel is in fluid connectivity to the first surface of the porous scaffold. The porous scaffold has a second microfluidic outlet channel, wherein the second microfluidic outlet channel is in fluid connectivity to the second surface of the porous scaffold.

The polymeric chip can have one or more porous scaffolds. In one embodiment, the polymeric chip can have a plurality of porous scaffolds. The porous scaffolds within the chip may share the microfluidic inlet channel. In addition, the porous scaffolds within the chip may share the microfluidic outlet channel. Alternatively, one or more porous scaffolds may have their separate and individual microfluidic outlet channel.

In one embodiment, the polymeric chip of the present invention includes a first porous scaffold and a second porous scaffold in the chip, which is separated from the first porous scaffold. The first porous scaffold is connected to the second porous scaffold through a first microfluidic channel. The chip has a second microfluidic channel inlet to the first porous scaffold and a third microfluidic channel outlet from the second porous scaffold.

Embodiments of the present invention relate to polymeric chips, which can be used as three-dimensional micro-scale engineered tissue model systems for drug discovery and development and to the methods for making and using the chips. For cancer drug selection, for example, there can be two advantages for using three-dimensional tissue model systems described herein: (1) three-dimensional tissue models better mimic in vivo cancer progression and therefore allow one to study tumor-stroma interaction and tumor-extracellular matrix (ECM) interactions; and (2) three-dimensional tissue models decrease the use of in vivo tumor models and the use of animals for drug selection studies.

It is well established that in vivo cancer progression is modulated by the host and the tumor micro-environment, including the stromal cells and extracellular matrix (ECM). For example, stromal cells were found being able to convert benign epithelial cells to malignant cells. ECM was found to affect the tumor formation. Both phenomena could only be observed in three-dimensional tissues. There is growing evidence that cells growing in three-dimensional cultures are more resistant to cytotoxic agents than cells in mono layers. Therefore, a three-dimensional tissue model is a better simulation for the original growth characteristics of cancer cells and better reflects the real drug sensitivity of in vivo tumors.

In addition to drug discovery and development, three-dimensional tissue models described herein are also useful in basic and clinical research. For example, three-dimensional tissue models can be used to research the mechanism of tumorigenesis. Unlike animal models that are less amenable to large scale genetic studies, three-dimensional tissue models enable researchers both to perform genetic manipulations and to observe some of the biological changes that the genes bring about. In addition, three-dimensional tissue models can be used to research the hematopoietic differentiation efficacy of embryonic stem cells.

Specifically, embodiments of polymeric chips described herein have one or more three-dimensional porous scaffolds and connecting microfluidic channels to simulate the real biological environment of living cells. The porous scaffolds allow three-dimensional cell culture of various types of cells so that tissue specific architecture and function can be maintained.

Any suitable polymeric material can be used to manufacture the polymeric chip of the present invention. The material can be biodegradable or non-biodegradable. The material can preferably be a biocompatible material. Representative material that is useful in the present invention includes (PMMA)

poly(methyl methacrylate), (PLA) polystyrene, poly(lactic acid), and (PLGA) poly(lactic-co-glycolic acid).

In one embodiment, the porous scaffolds of the polymeric chip have a pore size from about 50 μm to about 200 μm. In one embodiment, the porous scaffolds of the polymeric chip have a pore size from about 70 μm to about 200 μm. In one embodiment, the porous scaffolds of the polymeric chip have a pore size from about 100 μm to about 200 μm. The average pore size diameter of any two or more porous scaffolds within a single chip can be the same or different.

The porous scaffolds can be used as cell culture scaffolds. Therefore, the porous scaffolds can include living cells. In one embodiment, the first porous scaffold comprises a plurality of first living cells and the second porous scaffold comprises a plurality of second living cells. The living cells cultured in the first porous scaffold can be same or different from the living cells cultured in the second porous scaffold. In one embodiment, the first porous scaffold comprises liver cells and the second porous scaffold comprises cancer cells.

FIG. 4 shows one embodiment of a representative polymeric chip of the present invention, a three-dimensional tissue model system, which mimics a two-organ tissue model system of a liver and cancer.

It has been well established that the liver metabolism plays an important role in drug responses at the individual patient level. The activity of human cytochrome P450 isoenzymes (CYPs) is a crucial factor for determining therapeutic efficacy, safety, and inter-individual variability of drug responses. Therefore, the variability of drug metabolism in the liver should be considered carefully in the drug development process. In clinical studies, there are often subpopulations of patients who show an ultra-rapid, extensive metabolic activity for a drug, while others show a poor metabolic activity (e.g., due to CYP2C8 and CYP3A4 genotypes). Therefore, a two-organ model system mimicking the physiological environment of a liver and cancer is useful to study the liver metabolic effects on cancer drugs.

As shown in FIG. 4, the three-dimensional tissue model system 200 has a first porous scaffold 205 and a second porous scaffold 210 that are separate and distinct from each other. Each porous scaffold includes a porous region having interconnected open-celled pores. Each porous scaffold defines a perimeter that is bound by nonporous polymer material. The two porous scaffolds 205 and 210 are connected with a first microfluidic channel 220 underneath. The channel 220 connects the lower surfaces of each porous scaffold together. A second microfluidic channel inlet 230 is connected only to the first porous scaffold 205. A third microfluidic channel outlet 240 is connected only to the second porous scaffold 210. In addition, the three-dimensional tissue model system has a top cover plate 250 and a bottom cover plate 260 that respectively covers the upper and lower surface of each porous scaffold, but allowing passage-ways that serve as the microfluidic channels.

Figure 5A:
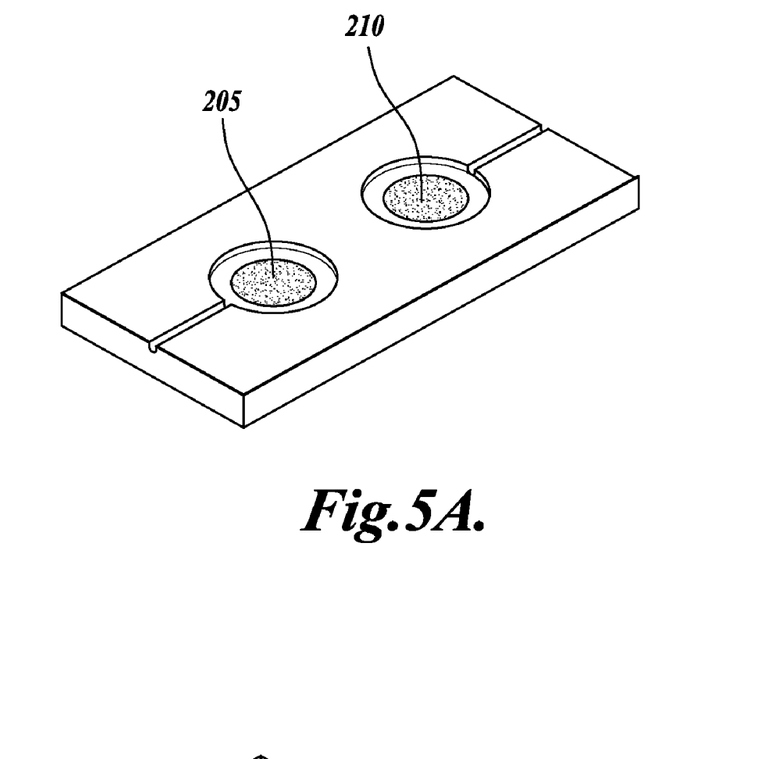
Figure 5B:
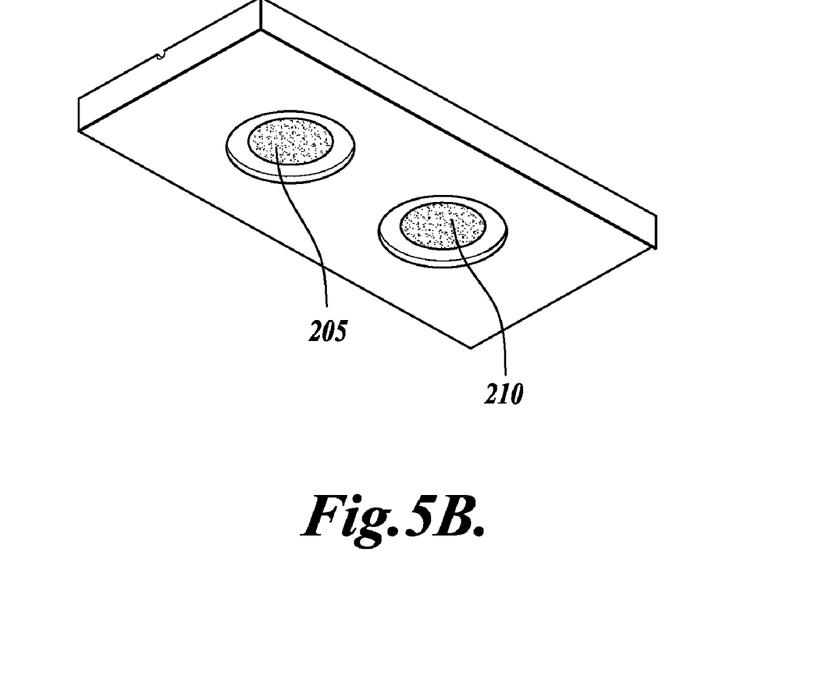

FIG. 5 shows the top and bottom view of the three-dimensional tissue model system 200 with porous scaffolds 205 and 210.

To mimic the delivery of drugs through the blood stream and the effects of the liver metabolism on drug responses, the three-dimensional tissue model system 200 has a circulating microfluidic channel including 230, 220, and 240 connecting two three-dimensional tissue scaffolds, porous scaffolds 205 and 210, with growing liver cells and cancer cells separately.

While seeding, liver cells and cancer cells can be separately injected into the two porous scaffolds 205 and 210 from the inlet 230 and the outlet 240. The cells will be allowed 24 hours to attach to the scaffold surfaces. After cell attachment, perfusion with culture media will begin to promote cell growth and proliferation. During perfusion, the culture media inflow will be injected from the inlet 230 onto the upper surface of the porous scaffold 205. The culture media will flow through the thickness of the porous scaffold 205 and exit the porous scaffold 205 from the lower surface and into the microfluidic channel 220. Next, the media will flow up from the channel 220 into the porous scaffold 210 where it will exit the upper surface and enter the microfluidic channel 240. Drugs can be delivered in the same fashion after three to five days of cell culture depending on the cell types. The cell culture will be conducted in an incubator. A peristaltic pump may be used to provide perfusion.

The polymeric chip, such as the three-dimensional tissue model system 200, has the advantage of replacing or reducing the need for costly clinical trials. In addition, the system may allow improvement and personalization of anticancer agent therapy, i.e., drug dosage selection for individuals. For example, the three-dimensional tissue model system allows clinicians to select the best drug dosage for people with certain CYP genotypes. Moreover, this system can be used to predict drug-drug interactions in a combination of anticancer agent regimes.

Figure 6A:
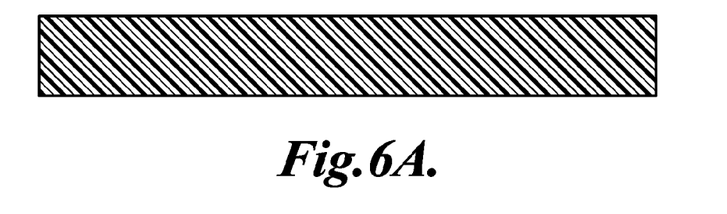
FIGS. 6A-6E schematically illustrate the fabrication process of a representative polymeric chip in accordance with one embodiment of the present invention.
Figure 6B:
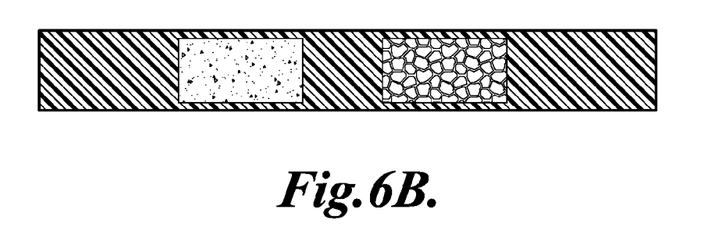
Figure 6C:
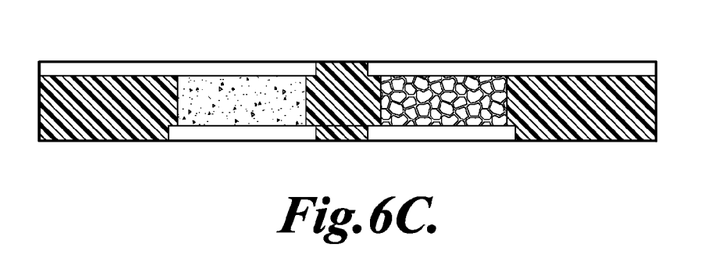

FIGS. 6A-E schematically illustrate the fabrication process of the polymeric chip 200. FIG. 6A shows a poly(methyl methacrylate) chip. First, the poly(methyl methacrylate) chip is selectively foamed to create two separate and distinct porous scaffolds 205 and 210 of controlled pore sizes within the same chip, as shown in FIG. 6B. The pores are preferably interconnected open-celled pores made by partially saturating the polymeric chip 200, and applying high intensity ultrasound energy onto the partially saturated polymeric chip. Then, micro milling is performed to shape the porous scaffolds and build the connecting microfluidic channels, as shown in FIG. 6C. As best seen in FIGS. 5A and 5B, micro milling produces wells surrounding each upper and lower surface of each porous scaffold, wherein each well is of a diameter larger than the diameter of the porous scaffold. After micro milling, cell retaining membranes 280 and 290 and the bottom cover plate 260 are bound to the polymeric chip. The cell retaining membranes 280 and 290 are bound to the bottom of the porous scaffolds 205 and 210. The cell retaining membranes allow nutrient to pass through, but not the cells. The retaining membranes may or may not be needed depending on whether the three-dimensional porous scaffold will hold the cells inside long enough such that the cells will attach to the scaffold surface, instead of falling through to the bottom of the microfluidic channel.

Figure 6D:
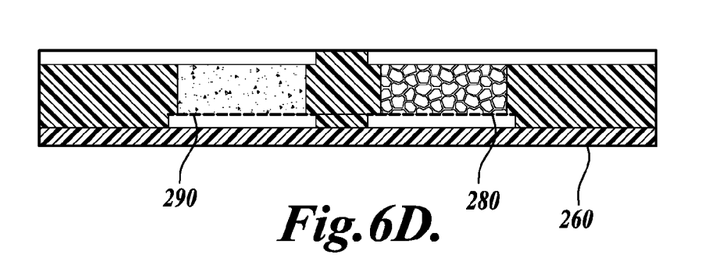
Figure 6E:
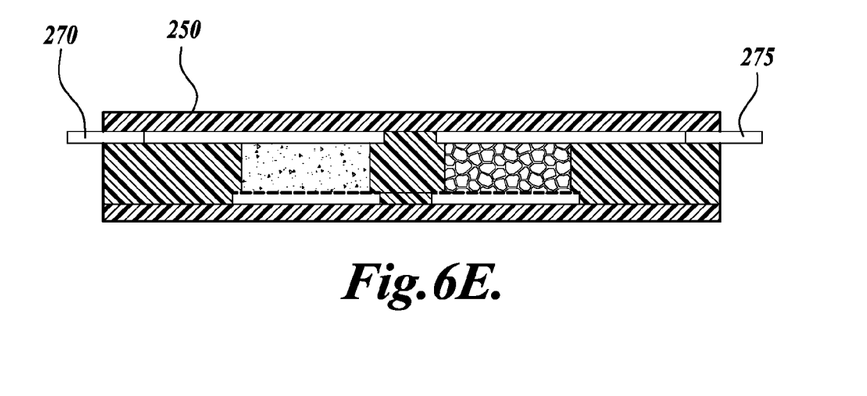

The bottom cover plate 260 and the top cover plate 250 can be bound to the polymeric chip with double-sided adhesive acrylic tape. The retaining membranes 280 and 290, the microfluidic channel inlet tubing 270, and the microfluidic channel outlet tubing 275 can be bound with acrylic glue. When bonding the retaining membranes 280 and 290 to the bottom of the porous scaffolds 205 and 210, the glue may be applied to the edge to avoid sealing the pores on the center of both the scaffolds and the membranes. Alternatively, diffusion bonding can be used to bond the retaining membranes.

The polymeric chip can be discarded after a single use. Therefore, destructive sectioning can be performed to evaluate cell attachment and growth in the three-dimensional porous scaffolds.

In another embodiment, a polymeric chip may include two or more porous scaffolds in the chip. Each porous scaffold includes a first surface and a second surface. The first surface is opposite to the second surface. The first microfluidic inlet channel is in fluid connectivity to the first surface of each porous scaffold through a first microfluidic inlet channel. The second microfluidic outlet channel is in fluid connectivity to the second surface of at least one porous scaffold through a second microfluidic outlet channel.

The porous scaffolds in the polymeric chip can share a common microfluidic channel outlet, have individual microfluidic channel outlet, or some porous scaffolds can share a common microfluidic channel outlet and others can have individual microfluidic channel outlet. An individual microfluidic channel outlet allows the collection of fluid outflow from individual porous scaffold for analysis. In one embodiment, the second microfluidic outlet channel is in fluid connectivity to the second surface of each porous scaffold. In one embodiment, the polymeric chip further comprises a third microfluidic outlet channel, wherein the third microfluidic outlet channel is in fluidic connectivity to the second surface of at least one porous scaffold.

Each porous scaffold of the polymeric chip comprises a 3-dimensional volume having an average pore size from about 50 μm to about 200 μm. The pore size at each porous scaffold can be different.

In one embodiment, each porous scaffold of the polymeric chip comprises living cells.

Figure 7:
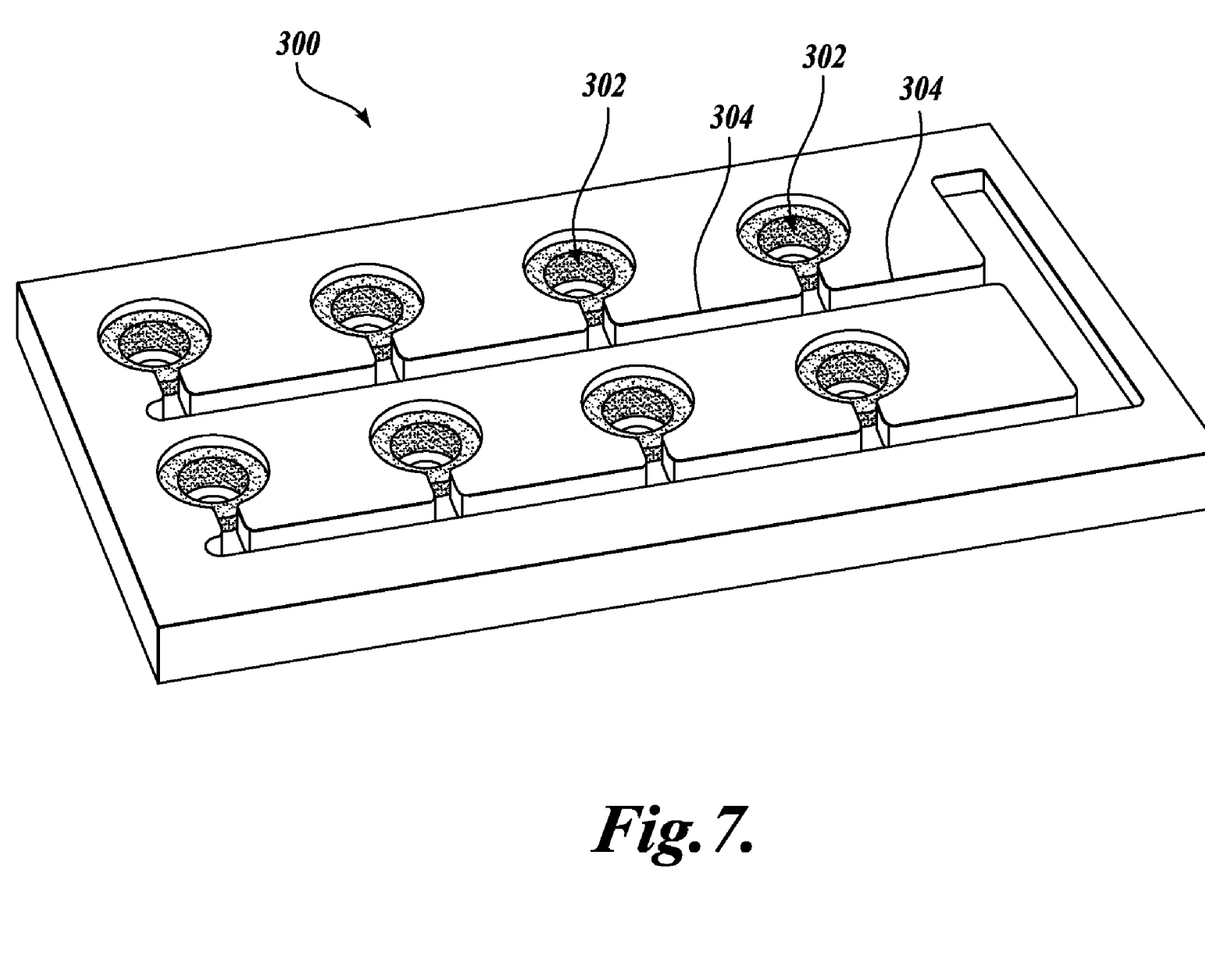
FIG. 7 shows a representative polymeric chip for creating a three-dimensional cell culture.

A representative polymeric chip 300 is shown in FIG. 7. The porous scaffolds 302 can be connected with microfluidic channels 304. Living cells can be seeded on the porous scaffolds, while nutrients can be supplied through the channels.

FIG. 8 illustrates a cross-sectional view of a polymeric chip. The polymeric chip 300 contains three porous scaffolds 310, 320, and 330 that are separate and distinct from each other. Each porous scaffold includes a lower surface and an upper surface. Each of the lower and upper surfaces extends over the entire area of the porous scaffold. A first microfluidic inlet channel 340 is in fluid connectivity with each lower surface of each porous scaffold. A second microfluidic outlet channel 350 is in fluid connectivity to each upper surface of each porous scaffold. The cell culture medium in-flow is from the lower surface so that each of the porous scaffolds 310, 320, and 330 can be submerged in the culture medium.

In one embodiment, the polymeric chip 300 includes three distinct porous structures. The first two 310, 320 have a different pore size and can be used to test the pore size effect on cell behavior. The third porous structure 330 includes a well 335 and could be used for co-culture of different cells. In one embodiment, at least one scaffold on the polymeric chip includes a well. The scaffold having a well may be formed from a lower section surrounded by upright walls to form a cavity in the middle. For example, the outer layer of the well can be seeded with stromal cells, and the inner center of the well can be seeded with cancer cells. This model can be used to study the stromal-cancer cell interaction and drug penetration and resistance.

In one embodiment, one or more porous scaffolds in the chip can have separate and individual microfluidic outlet channel(s), which allows the collection of the fluid sample from individual porous scaffold for analysis.

The porous scaffolds in the polymeric chips of the present invention can be created using the selective high intensity focused ultrasound (HIFU) system and method described above. The selective HIFU process creates porous structures with controlled pore sizes and at designed locations on the polymeric chips. The selective foaming technique uses high intensity focused ultrasound to selectively heat and implode gas-impregnated polymers to generate porous structures that make suitable scaffolds. Original polymer specimens are first loaded into a pressure vessel filled with high pressure inert gas. Over time, gas molecules dissolve in the polymer matrix and yield supersaturated polymer samples. After the equilibrium gas concentration is reached the samples are taken out of the vessel and loaded onto a HIFU foaming system for ultrasound insonation.

Not wanting to be limited by the theory, it is believed that there are two mechanisms that could contribute to the foaming process during HIFU insonation of gas saturated polymers. One is the ultrasound cavitation effect, which is enhanced by much more gas molecules inside the polymer matrix due to saturation. The second is the ultrasound heating effect, which raises the temperature of the polymer matrix. When subjected to elevated temperature, the saturated polymer sample becomes thermodynamically instable and undergoes phase separation. The result is the forming of gas bubbles and thus foaming of the polymer. Both mechanisms result in rapid and effective HIFU foaming of saturated polymers.

Figure 9A:
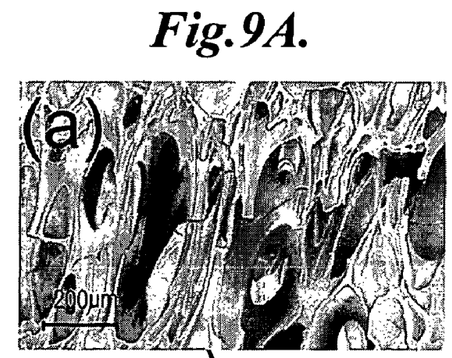
FIGS. 9A-C show an exemplary polymeric chip with multiple porous scaffolds, wherein the porous scaffolds have different pore sizes.
Figure 9B:
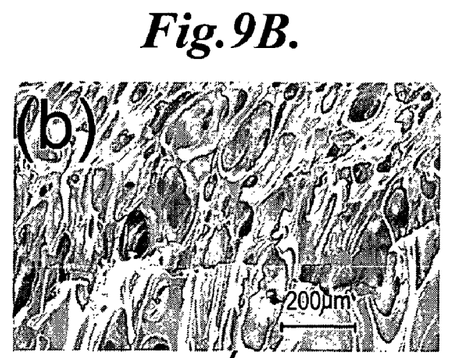
Figure 9C:
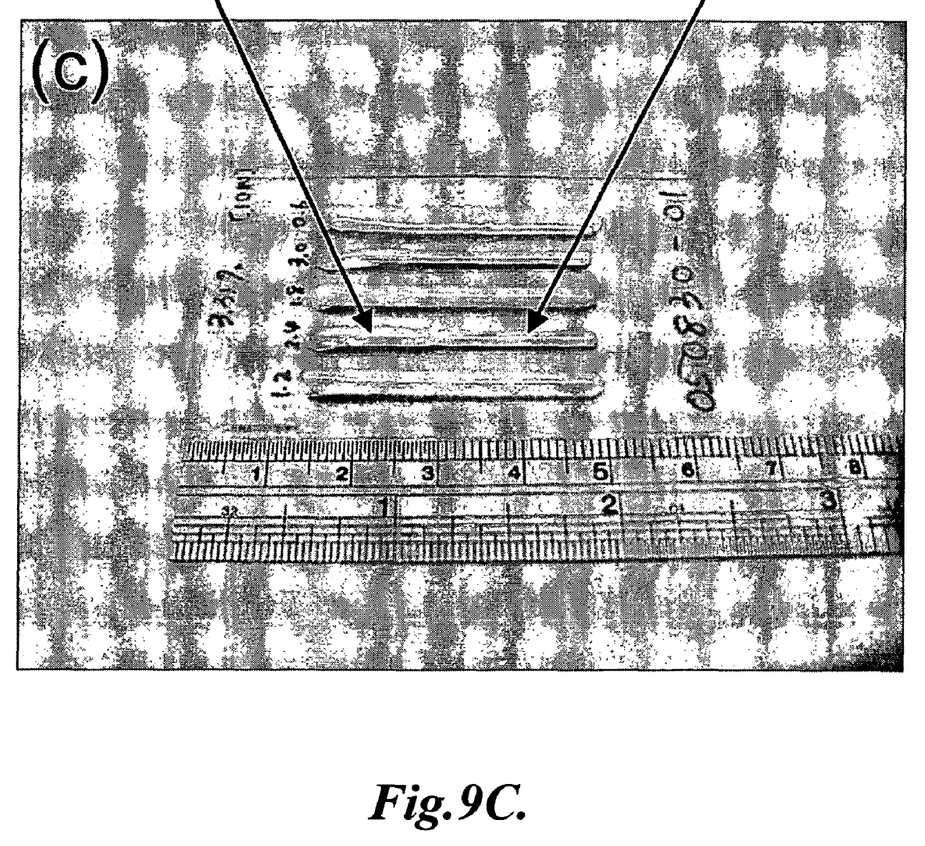

An exemplary polymeric chip with multiple porous scaffolds is shown in FIGS. 9A, 9B, and 9C. FIG. 9C shows an overview of the polymeric chip. FIGS. 9A and 9B demonstrate that the porous scaffolds on the chip have different pore sizes.

The porous scaffold can be machined using a micro milling process to create a designed shape. The micro milling process is a regular mechanical milling process, except the position accuracy, the spindle runout error, and the size of the mill cutter are all much smaller than a conventional milling machine. The micro milling process is used for creating micro holes and channels to connect the foamed regions, i.e., porous scaffolds. In this manner, complex biological systems involving different tissue or organs can be simulated.

In another aspect, the present invention provides methods for assaying a compound activity.

In one embodiment, the method includes the step of providing a polymeric chip. The chip has a first porous scaffold and a second porous scaffold in the chip, which is separated from the first porous scaffold. The first porous scaffold is connected to the second porous scaffold through a first microfluidic channel. The chip has a second microfluidic channel inlet to the first porous scaffold and a third microfluidic channel outlet from the second porous scaffold. A plurality of first living cells are seeded in the first porous scaffold to provide a first cell culture. A plurality of second living cells are seeded in the second porous scaffold to provide a second cell culture. A compound is dissolved in a cell culture medium to provide a liquid medium. The liquid medium is flowed sequentially through the second microfluidic channel inlet, the first cell culture, the first microfluidic channel, the second cell culture, and the third microfluidic channel outlet to provide an assay solution.

In one embodiment, the first cell culture comprises liver cells and the second cell culture comprises cancer cells.

In one embodiment, the method of the present invention further comprises the step of analyzing the second cell culture to determine the inhibitory activity of the compound on the cancer cells.

In one embodiment, the method of the present invention further comprises the step of analyzing the assay solution.

In another embodiment, the method includes the step of providing a polymeric chip. The chip includes at least one porous scaffold in the chip. The porous scaffold includes a first surface and a second surface. The first surface is opposite from the second surface. A first microfluidic inlet channel is in fluid connectivity to the first surface of the porous scaffold. A second microfluidic outlet channel is in fluid connectivity to the second surface of the porous scaffold. A plurality of living cells are seeded in the porous scaffold to provide a cell culture. A compound is dissolved in a cell culture medium to provide a liquid medium. The liquid medium is flowed through the first microfluidic inlet channel, the cell culture, and the second microfluidic outlet channel to provide an assay solution.

In one embodiment, the cell culture comprises liver cells. In one embodiment, the cell culture comprises cancer cells. In one embodiment, the cell culture comprises both stromal cells and cancer cells.

In one embodiment, the method further comprises the step of analyzing the cell culture to determine the inhibitory activity of the compound on the cells.

In another embodiment, the method includes the step of providing a polymeric chip. The chip includes two or more porous scaffolds. Each porous scaffold includes a first surface and a second surface. The first surface is opposite to the second surface. A first microfluidic inlet channel is in fluid connectivity with the first surface of each porous scaffold. A second microfluidic outlet channel is in fluid connectivity to the second surface of at least one porous scaffold. The second microfluidic outlet channel may be in fluid connectivity to the second surface of each porous scaffold. The chip may further include a third microfluidic outlet channel, which is in fluidic connectivity to the second surface of at least one porous scaffold.

Living cells may be seeded in the porous scaffolds to provide cell cultures. The two or more porous scaffolds may include the same or different living cells. A plurality of first living cells are seeded in a first porous scaffold to provide a first cell culture. A plurality of second living cells are seeded in a second porous scaffold to provide a second cell culture. A compound is dissolved in a cell culture medium to provide a liquid medium. The liquid medium is flowed through the first microfluidic inlet channel, simultaneously through the cell cultures, through the second microfluidic outlet channel, or simultaneously through the third microfluidic outlet channel if applicable, to provide one or more assay solutions.

EXAMPLE

Figure 10A:
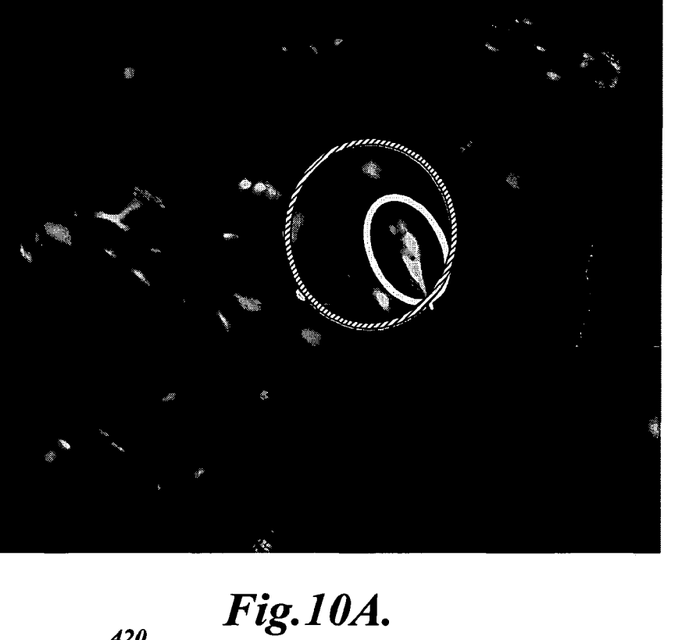
Figure 10B:
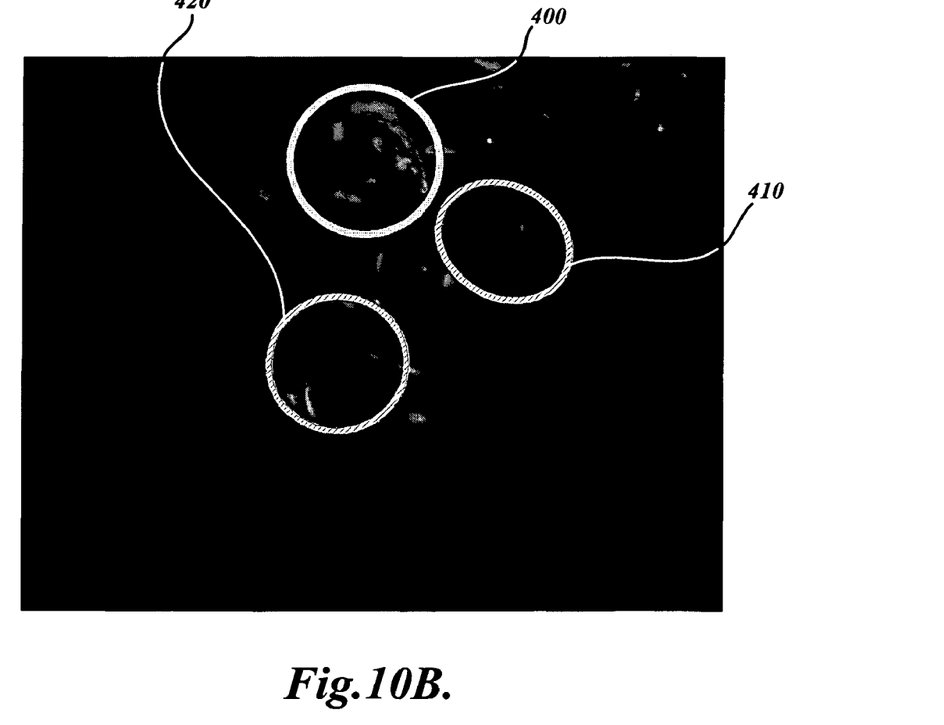

A cell culture study was conducted using the fabricated porous scaffolds. Scaffolds with different pore sizes (70 μm and 200 μm) were chosen for the cell culture study to demonstrate their effects on cellular response and cell growth behavior. Human aortic (SMCs) smooth muscle cells of Passage 4 were taken out of liquid nitrogen and passaged into T75 flasks until full confluence was reached. Fabricated porous poly(methyl methacrylate) specimens were sterilized under UV light for 15 minutes and then incubated with fetal bovine serum overnight. Approximately 75,000 cells were seeded into a 12-well plate, each containing one poly(methyl methacrylate) specimen. Cells were cultured in Dulbecco's Modified Eagle Medium (DMEM) for 5 days and then processed for live/dead stain for migration and viability study. FIGS. 10A and 10B show the live/dead staining results of smooth muscle cells on the porous scaffold. Live cells are shown as gray and white spots. Circles 410 and 420 correspond to pores in the porous polymer and circle 400 correspond to live cells.

Cells were viable on the porous scaffold. This illustrates the biocompatibility of the selective ultrasound foaming process. Moreover, the morphology of the cells differed in the large pores compared to that in the smaller pores. In the 200 μm pores, shown in FIG. 10A, the cells tended to lie on the walls of the pores, whereas in 70 μm pores shown in FIG. 10B, the cells tended to cling on to the edges of the pores and spread out more. Therefore, the behavior of cell growth can be manipulated by selection of the pore size.

While illustrative embodiments have been illustrated and described, it will be appreciated that various changes can be made therein without departing from the spirit and scope of the invention.

The embodiments of the invention in which an exclusive property or privilege is claimed are defined as follows:

1. A polymeric chip, comprising,
   at least one porous scaffold, wherein the porous scaffold is formed from the polymeric chip and is localized within a portion of the polymeric chip, wherein the porous scaffold includes a first surface and a second surface, and wherein the first surface is opposite from the second surface;
   a first microfluidic inlet channel, wherein the first microfluidic inlet channel is in fluid connectivity with the first surface of the porous scaffold; and
   a second microfluidic outlet channel, wherein the second microfluidic outlet channel is in fluid connectivity with the second surface of the porous scaffold.

2. The polymeric chip of claim 1, wherein each surface is the area defined by either the upper or lower perimeter of the porous scaffold.

3. The polymeric chip of claim 1, wherein the porous scaffold has a pore size from about 50 μm to about 200 μm.

4. The polymeric chip of claim 1, wherein the porous scaffold comprises a plurality of living cells.

5. The polymeric chip of claim 1, wherein the chip comprises polymethyl methacrylate, polystyrene, poly(lactic acid), or poly(lactic/glycolic acid).

6. A polymeric chip, comprising:
   two or more porous scaffolds, wherein each porous scaffold is formed from the polymeric chip and is localized within a portion of the polymeric chip, wherein each porous scaffold includes a first surface and a second surface, and wherein the first surface is opposite to the second surface;
   a first microfluidic inlet channel, wherein the first microfluidic inlet channel is in fluid connectivity with the first surface of each porous scaffold; and
   a second microfluidic outlet channel, wherein the second microfluidic outlet channel is in fluid connectivity with the second surface of at least one porous scaffold.

7. The polymeric chip of claim 6, wherein the second microfluidic outlet channel is in fluid connectivity to the second surface of each porous scaffold.

8. The polymeric chip of claim 6, further comprising a third microfluidic outlet channel, wherein the third microfluidic outlet channel is in fluidic connectivity to the second surface of at least one porous scaffold.

9. The polymeric chip of claim 6, wherein each porous scaffold comprises a 3-dimensional volume comprising pores having an averages size from about 50 μm to about 200 μm.

10. The polymeric chip of claim 6, wherein each porous scaffold comprises living cells.

11. The polymeric chip of claim 6, wherein a first porous scaffold comprises liver cells and a second porous scaffold comprises cancer cells.

12. A polymeric chip, comprising,
   at least one porous scaffold, wherein the porous scaffold is formed from the polymeric chip and is localized within a portion of the polymeric chip, wherein the porous scaffold includes a first surface and a second surface, wherein the first surface is opposite from the second surface, and wherein the porous scaffold includes a well having a bottom surface surrounded by upright walls and formed within the porous scaffold;

a first microfluidic inlet channel, wherein the first microfluidic inlet channel is in fluid connectivity with the first surface of the porous scaffold; and a second microfluidic outlet channel, wherein the second microfluidic outlet channel is in fluid connectivity with the second surface of the porous scaffold.

13. A method for providing an assay solution, comprising,
(a) providing a polymeric chip, comprising,
a first porous scaffold in the chip;
a second porous scaffold in the chip, which is separated from the first porous scaffold, wherein the first porous scaffold and the second porous scaffold are formed from the polymeric chip and are localized within a portion of the polymeric chip;
a first microfluidic channel connecting the first porous scaffold to the second porous scaffold;
a second microfluidic channel inlet to the first porous scaffold; and
a third microfluidic channel outlet from the second porous scaffold;
(b) seeding a plurality of first living cells in the first porous scaffold to provide a first cell culture;
(c) seeding a plurality of second living cells in the second porous scaffold to provide a second cell culture;
(d) dissolving a compound in a cell culture medium to provide a liquid medium;
(e) flowing the liquid medium sequentially through the second microfluidic channel inlet, the first cell culture, the first microfluidic channel, the second cell culture, and the third microfluidic channel outlet to provide an assay solution.

14. The method of claim 13, wherein the first cell culture comprises liver cells and the second cell culture comprises cancer cells.

15. The method of claim 14, further comprising analyzing the second cell culture to determine the inhibitory activity of the compound on the cancer cells.

16. The method of claim 15, further comprising analyzing the assay solution.

17. A method for providing an assay solution, comprising,
(a) providing a polymeric chip, comprising:
at least one porous scaffold, wherein the porous scaffold is formed from the polymeric chip and is localized within a portion of the polymeric chip, wherein the porous scaffold includes a first surface and a second surface, and wherein the first surface is opposite from the second surface;
a first microfluidic inlet channel, wherein the first microfluidic inlet channel is in fluid connectivity with the first surface of the porous scaffold; and
a second microfluidic outlet channel, wherein the second microfluidic outlet channel is in fluid connectivity to the second surface of the porous scaffold;
(b) seeding a plurality of living cells in the porous scaffold to provide a cell culture;
(c) dissolving a compound in a cell culture medium to provide a liquid medium;
(d) flowing the liquid medium through the first microfluidic inlet channel, the cell culture, and the second microfluidic outlet channel to provide an assay solution.

18. The method of claim 17, wherein the cell culture comprises liver cells.

19. The method of claim 17, wherein the cell culture comprises cancer cells.

20. The method of claim 17, wherein the cell culture comprises both stromal cells and cancer cells.

21. The method of claim 17, further comprising analyzing the cell culture to determine the inhibitory activity of the compound on the cells.

* * * * *